United States Patent
Krall et al.

(10) Patent No.: US 11,434,457 B2
(45) Date of Patent: Sep. 6, 2022

(54) MULTIWELL IMAGING PLATE AND METHOD FOR INCUBATING NON-ADHERENT CELLS

(71) Applicant: CEMM FORSCHUNGSZENTRUM FUR MOLEKULARE MEDIZIN GMBH, Vienna (AT)

(72) Inventors: Nikolaus Krall, Vienna (AT); Gregory Vladimer, Vienna (AT); Berend Snijder, Basel (CH)

(73) Assignee: CEMM FORSCHUNGSZENTRUM FUR MOLEKULARE MEDIZIN GMBH, Vienna (AT)

( * ) Notice: Subject to any disclaimer, the term of this patent is extended or adjusted under 35 U.S.C. 154(b) by 488 days.

(21) Appl. No.: 16/098,291

(22) PCT Filed: May 3, 2017

(86) PCT No.: PCT/EP2017/060561
§ 371 (c)(1),
(2) Date: Nov. 1, 2018

(87) PCT Pub. No.: WO2017/191203
PCT Pub. Date: Nov. 9, 2017

(65) Prior Publication Data
US 2019/0062685 A1    Feb. 28, 2019

(30) Foreign Application Priority Data
May 4, 2016   (EP) .................................... 16168400

(51) Int. Cl.
*C12M 1/32*   (2006.01)
*B01L 3/00*   (2006.01)
*B01L 99/00*   (2010.01)

(52) U.S. Cl.
CPC ........... *C12M 23/12* (2013.01); *B01L 3/5085* (2013.01); *B01L 2200/0642* (2013.01);
(Continued)

(58) Field of Classification Search
CPC ..... B01L 2200/0642; B01L 2200/0647; B01L 2300/0829; B01L 2300/0851; B01L 3/5085; C12M 23/12
See application file for complete search history.

(56) References Cited

U.S. PATENT DOCUMENTS

| | | |
|---|---|---|
| 6,197,575 B1 | 3/2001 | Griffith et al. |
| 2003/0215941 A1 | 11/2003 | Campbell et al. |
| 2007/0141555 A1 | 6/2007 | Deutsch |

FOREIGN PATENT DOCUMENTS

| | | |
|---|---|---|
| WO | 02097029 | 12/2002 |
| WO | 2007035604 A2 | 3/2007 |
| WO | 11127945 | 10/2011 |

OTHER PUBLICATIONS

European Search Report dated Aug. 2, 2016 in corresponding application 16168400.6.
(Continued)

*Primary Examiner* — Lydia Edwards
(74) *Attorney, Agent, or Firm* — Seager, Tufte & Wickhem, LLP

(57) ABSTRACT

The invention relates to a multiwell imaging plate and a method for incubating non-adherent cells. The multiwell imaging plate includes multiple wells, at least some of the wells having a first chamber, a second chamber arranged on top of the first chamber, and a disturbance blocking structure provided between the first chamber and the second chamber. The first chamber is formed by one or more first sidewalls and a bottom wall while the second chamber is formed by one or more second sidewalls and includes an opening for introducing liquids. The disturbance blocking structure
(Continued)

includes at least one through hole that provides a liquid connection between the first and second chambers.

20 Claims, 6 Drawing Sheets

(52) U.S. Cl.
CPC .............. *B01L 2200/0647* (2013.01); *B01L 2300/0829* (2013.01); *B01L 2300/0851* (2013.01)

(56) References Cited

OTHER PUBLICATIONS

International Search Report and Written Opinion dated Jul. 11, 2017 in corresponding PCT application PCT/EP2017/060561.
Communication pursuant to Article 94(3) EPC, for Application No. 17726545.1, dated Mar. 19, 2020, 4 pages.
International Search Report and Written Opinion for International application No. PCT/US2006/36234, dated Jul. 16, 2008, 4 pages.

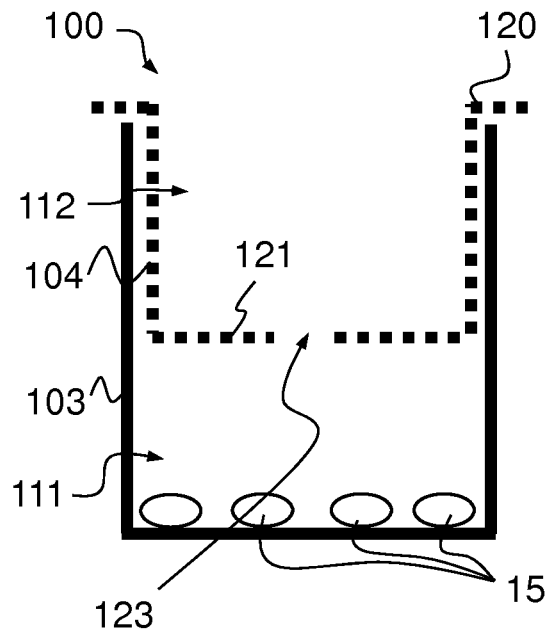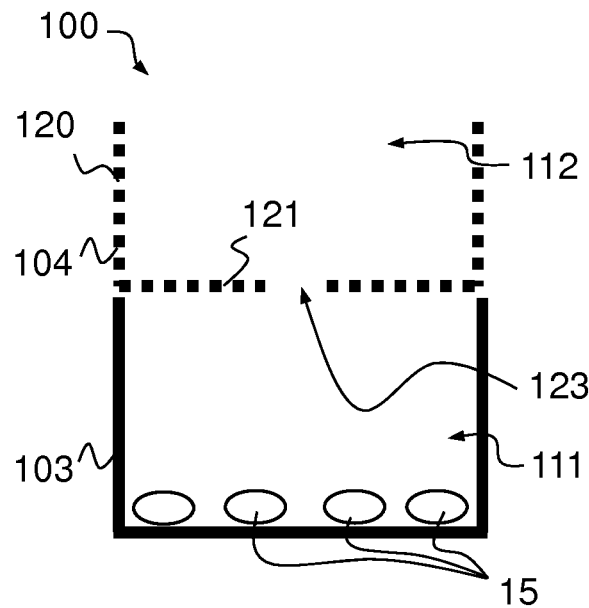
Fig. 3    Fig. 4
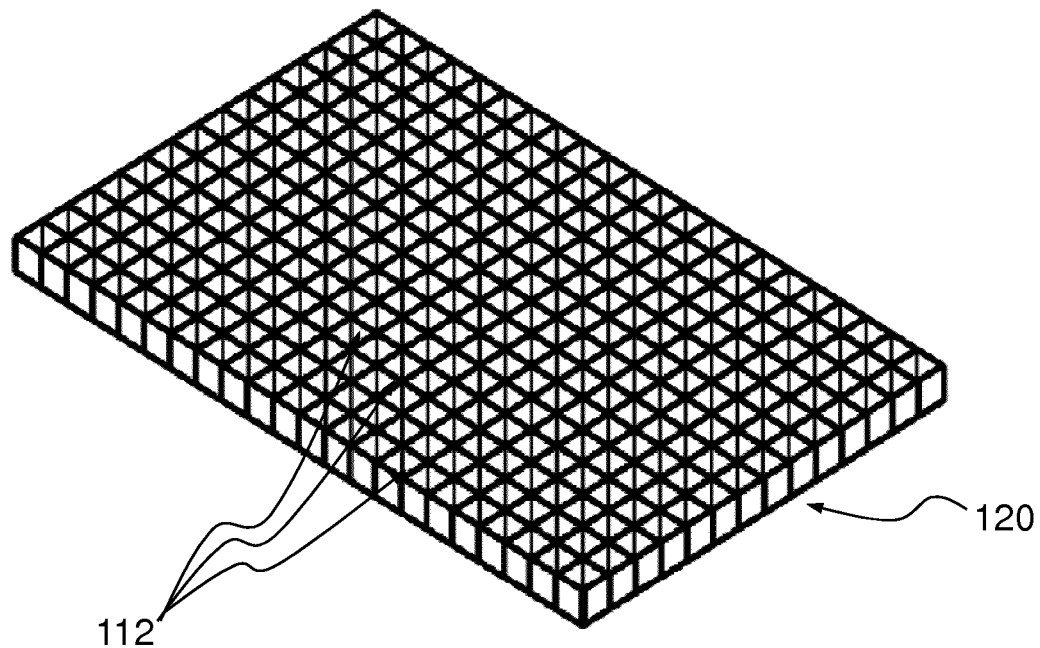
Fig. 5

MULTIWELL IMAGING PLATE AND METHOD FOR INCUBATING NON-ADHERENT CELLS

CROSS-REFERENCE TO RELATED APPLICATIONS

This application is a national stage filing under 35 U.S.C. 371 of international PCT application PCT/EP2017/060561, filed May 3, 2017 which claims priority to European Application No. 16168400.6, filed May 4, 2016, the entire disclosures of which are herein incorporated by reference.

The present invention relates to a cell incubation device and a method employing such device. In particular, the invention relates to a multiwell imaging plate and methods employing such plate. More specifically, the invention relates to a multiwell imaging plate and a method for incubating non-adherent cells, in particular as a monolayer. The cell incubation device and method of the present invention can be used to obtain cell monolayers that are more evenly formed and/or better suited for image analysis. Further, the cell incubation device and method of the present invention can be used to reduce perturbation to the monolayer due to the addition or removal of reagents to or from the monolayer.

Co-pending WO 2016/046346 A1, the contents of which are hereby incorporated by reference in their entirety, discloses methods for culturing peripheral blood mononuclear cell (PBMC) monolayers and bone-marrow cell monolayers. Also disclosed are methods using such PBMC or bone-marrow cell monolayers, in particular screening methods for determining a response or lack of response of a disease to therapeutic agents.

When using the methods disclosed in WO 2016/046346 A1, it has been discovered by the present inventors that the cells may, in some instances, have a tendency to cluster in regions close to sidewalls of devices in which the cells are incubated. This may pose a challenge for the screening methods of WO 2016/046346 A1 since individual cells may be more difficult to discern when performing image analysis. Furthermore, co-pending EP application no. 17 15 7806.5, the contents of which are hereby incorporated by reference in their entirety, discloses measuring cell-cell interaction propensities in cell monolayers. Also such measurements may be affected for the same reasons as mentioned above.

US 2007/0141555 A1 describes devices for the study of cells including a vessel with a current dampener including a damping component substantially disposed within the vessel. The damping component is said to reduce or eliminate currents formed by the addition of materials such as liquids to the vessel to prevent the movement of cells resting on the bottom surface of the vessel. These devices, however, have a structure that makes them difficult to manufacture and are also not believed to satisfactorily provide the intended type of monolayers.

In view of the above, it is an object of the present invention to provide a cell incubation device and an incubation method that achieves a more even formation of monolayers. In particular, it is an object of the present invention to provide a cell incubation device and an incubation method that reduces the agglomeration of cells along the sidewalls of the device. It is also an object of the present invention to provide a cell incubation device that is economical to manufacture.

A further object of the invention is to provide a cell incubation device and method that is more user-friendly.

A further object of the invention is to provide a cell incubation device and method which allows to perform screenings on relatively small cell populations.

The above-mentioned objects are achieved by the improved cell incubation device and method according to the claims. Further aspects, improvements and variations are disclosed in the figures and in the description.

According to a first aspect, the invention relates to a cell incubation device for incubating cells. The cell incubation device comprises a first chamber, the first chamber being formed by one or more first sidewalls and a bottom wall, a second chamber, the second chamber being formed by one or more second sidewalls, and a disturbance blocking structure that is provided between the first chamber and the second chamber to decrease disturbances, in particular currents, acting on the cells during incubation.

Throughout this disclosure, the term "incubation" should not necessarily be understood to imply that the cells have to remain in the cell incubation device for a minimum time period. In particular, cells isolated from a sample, placed in the cell incubation device and imaged are considered to be incubated on or in the device regardless of the time that the cells have been on or in the cell incubation device. Cell "incubation" could also be referred to as cell "culture" in the context of the present invention. The cells may, however, remain on or in the device for a certain time period, as discussed in more detail below. "Screening" may be understood, throughout this disclosure, as the testing of more than 10, more 100 or preferably more than several hundred or several thousand of active substances (e.g., biologicals and/or drugs) for their effects on cells.

The cell incubation device of the present invention is preferably suitable for incubating non-adherent cells as a monolayer. These cells may include blood cells, bone marrow cells, dissociated lymph node tissue, and/or hematopoietic stem cells. In the context of the present disclosure, they may be referred to summarily as peripheral blood mononuclear cells (PBMCs).

The first sidewalls may extend around and/or along the periphery of the first chamber. The second sidewalls may extend around and/or along the periphery of the second chamber.

The first chamber and/or the second chamber may define a cylindrical or non-cylindrical inner space. In particular, the first chamber and/or the second chamber may define a square or rectangular inner space. In other words, the first sidewalls and/or the second sidewalls may define a circle or a non-circular shape in a cross sectional plane that is horizontal and/or parallel to the bottom wall. The shape defined by the first and/or by the second sidewalls in a cross sectional plane that is horizontal and/or parallel to the bottom wall may be rectangular or square. Without wanting to be bound by theory, it is believed that such shape may be advantageous because it may contribute to reducing currents (e.g., vortexes) when adding liquids to the first and/or second chamber.

The cell incubation device may be a well for cultivating cells. Preferably, the cell incubation device is a multiwell plate with several or all of the plate's wells forming individual cell incubation devices according to the invention. The multiwell plate may have, for example, 96 wells, 384 wells or 1536 wells. However, the cell incubation device of the invention may also be a cell incubation flask or a cell incubation dish.

The disturbance blocking structure may include at least one through hole that provides a liquid connection between the first chamber and the second chamber. The through hole could also be referred to as a through opening.

The at least one through hole may be configured for a tip of a pipette being inserted therethrough. For example, the trough hole may allow the tip of a pipette to be inserted through the second chamber into the first chamber through said through hole. As apparent from the discussion below, this may be helpful for inserting cells into the first chamber and allowing them to settle in a monolayer. The through hole may be configured such that the pipette can be inserted through said through hole into the first chamber by moving it in a direction and/or along an axis that is substantially perpendicular to the bottom wall and/or substantially perpendicular to a plane in which the disturbance blocking structure extends. Alternatively or additionally, the through hole may be configured such that the pipette can be inserted through said through hole into the first chamber by moving it in a direction and/or along an axis that is substantially parallel to the first and/or second sidewalls. In other words, the pipette preferably can be inserted into the first chamber by moving it in a top-down (i.e., vertical) direction. The devices of US 2007/0141555 A1, for example as shown in FIG. 14 of this document, would not allow for an access of their first volume by means of a pipette tip and, in particular not in such vertical direction.

The at least one through hole could have any suitable shape and, for example, be circular, elliptical, square, rectangular or irregular in cross-section (in particular, in a horizontal cross sectional plane). The trough hole may be non-circular. The shape of the through hole could be configured to ensure sufficient evacuation of the first chamber when adding liquid to said fist chamber. For example, a non-circular shape may reduce the likelihood that a user inserts a pipette tip into the through hole in a manner that prevents sufficient air from leaving the first chamber while liquid is added thereto. The first chamber could be devoid of further air evacuation holes.

The through hole preferably is spaced from the first and/or second sidewalls, for example in a top view of the device. For example, the through hole could be formed in the center of the cell incubation device (in particular, in the center of the well, e.g., in a top view of the device). However, it could also be provided at or close to one of the sidewalls. Alternatively or additionally, the disturbance blocking structure could include at least one membrane and/or at least one foam and/or at least one porous matrix. Such membrane and/or foam could be configured to allow leakage of liquids and/or diffusion of certain substances therethrough during incubation. The membrane could be, for example, a microporous membrane. However, the disturbance blocking structure may be made from an essentially non-porous material.

The first chamber may include a first opening for injecting liquids into said first chamber. This first opening may be provided by the above-mentioned through hole.

The second chamber may include a second opening for injecting liquids into the first and/or into the second chamber. This second opening may be provided by an open top of the cell incubation device (in particular, an open top of the well). In a top view of the device, the second opening (specifically, the opening of said second chamber through which liquids may be added into the first and/or into the second chamber) may at least partially and preferably entirely overlap the first hole and/or the through hole. Alternatively or additionally, the second opening may be concentric with the first hole and/or with the through hole.

The second chamber may be arranged above and/or on top of the first chamber. In this case, the second chamber may form a top chamber while the first chamber forms a bottom chamber. Alternatively or additionally, the second chamber may be arranged adjacent and/or laterally of the first chamber. As will be understood by the skilled person, the terms "top" or "above" and "bottom" or "below" refer to a state in which the assembled cell incubation device is held in an upright position such that liquid(s) can be filled into the first and second chambers. The terms "laterally", "vertical", "horizontal", and "down" are also used with respect to this position of the device.

The at least one through hole may have a width of at least 0.5 mm, at least 0.8 mm or at least 1 mm. These values preferably relate to the smallest width of the through hole in a cross section that is horizontal and/or parallel to the bottom wall. In other words, when the through hole is circular, the diameter may be at least 0.5 mm, at least 0.8 mm or at least 1 mm. This may be particularly beneficial for introducing cells into the first chamber. For example, when the second chambers is arranged on top, such design facilitates the introduction of suitable pipettes through the disturbance blocking structure into the first chamber.

The at least one through hole may have a length of 2 mm or less, 1 mm or less, 0.5 mm or less, or 0.3 mm or less.

The bottom wall and/or an inner bottom surface of the cell incubation device may be substantially flat and/or horizontal. This may be beneficial for achieving a cell monolayer during incubation and preventing cell agglomerations. Optionally, the inner bottom surface of the device may be coated and/or treated so as to promote cell adhesion. For example, the inner bottom surface of the device may be coated with molecules or compounds that promote cell adhesion. Non-limiting examples of known agents that promote cell adhesion include, but are not limited to, polylysine, fibronectin or gelatin. The invention, however, does not exclude the use of devices that have not been treated and/or coated so as to promote cell adhesion. It may be preferable that the inner bottom surface of the device is not coated and/or microstructured.

The first sidewalls and/or the second sidewalls may extend in a substantially perpendicular manner with respect to the bottom wall. Preferably, an angle between the inner bottom surface of the device and the inner surface of the first and/or of the second sidewalls is 91° or less, 90.5° or less, 90° or less, 89.5° or less, or 89° or less.

The devices of the present invention are preferably configured to allow imaging of the cells directly in the device, in particular by standard high throughput microscopy i.e., confocal and/or fluorescent confocal and/or bright field microscopy. For this purpose, the bottom wall may be translucent, preferably transparent, at least in part or entirely. The bottom wall may be made, for example, of polycarbonate and/or glass.

The one or more first sidewalls surrounding the first chamber and/or the one or more second sidewalls surrounding the second chamber may be made of a material that absorbs light strongly. In particular, the one or more first sidewalls and/or the one or more second sidewalls may be made of a dark (e.g., black) material. This may reduce interference during imaging. For example, crosstalk and light scattering may be reduced, thus minimizing background fluorescence and/or background optical interference during fluorescence imaging. The one or more first sidewalls and/or the one or more second sidewalls may be made of polystyrene, in particular black polystyrene, acrylnitril-butadien-stytrol (ABS), in particular black ABS, and/or polypropylene, in particular black polypropylene.

The disturbance blocking structure could equally be made of a dark (e.g., black) and/or light absorbing material to reduce interference during imaging.

The material used for the disturbance blocking structure may be polymeric, for example, polystyrene, acrylonitrile butadiene styrene, PTFE, or silicone. The material used may also be and/or comprise at least one porous membrane and/or at least one gel, such as for example at least one hydrogel.

The disturbance blocking structure of the invention may be provided by an intermediate floor that is arranged in the device. The intermediate floor may protrude into an interior space of the device (e.g., into an interior space of the well and/or into an interior space formed by the first and/or by the second sidewalls) from at least a portion of the device's periphery (in particular, from the periphery of the interior space). Preferably, the intermediate floor extends along the entire periphery of the inner space. The intermediate floor may protrude from the first sidewalls and/or from the second sidewalls into the interior space. Preferably, the intermediate floor protrudes at least 0.3 mm, at least 0.5 mm or at least 0.7 mm from the respective sidewall into the interior space. The intermediate floor could also be referred to as a protrusion or rim extending at least partially or entirely around the periphery of the interior space. The periphery of the intermediate floor may directly be connected and/or integrally formed with the first and/or second sidewalls. Measured from the bottom wall, the intermediate floor may connect to the first and/or second sidewalls at $3/4$ or less, ⅝ or less, or $1/2$ or less, $1/4$ or less of the device's total height.

The through hole may be provided in the intermediate floor. For example, the through hole may extend through the intermediate floor. For example, FIG. 14 of US 2007/0141555 A1 shows a current dampener inside a vessel with an opening that is not provided in a bottom cover of the current dampener.

The first and/or second side walls may be devoid of through holes.

The disturbance blocking structure (in particular, the intermediate floor) may be solid and/or self-supporting. In other words, the material used for and/or the structure of the disturbance blocking structure may be such that the disturbance blocking structure does not or does not substantially bend under its own weight, even if it lacks further support elements (such as for example a support frame and/or support ribs). Accordingly, the disturbance blocking structure may be devoid of a support frame and/or devoid of support ribs.

The intermediate floor may extend in a substantially horizontal manner and/or parallel to the bottom wall. It may also extend substantially perpendicularly to the first and/or to the second sidewalls. The intermediate floor may, however, also extend upwardly from the sidewalls, for example, upwardly from the sidewalls towards the through hole. In this case, an angle between the second sidewalls and the intermediate floor in a vertical cross section of the device preferably is at least 70°, at least 80°, at least 85°, or at least 87°. The intermediate floor may thus extend upwardly at an angle of less than 20°, less than 10°, less than 5°, or less than 3° with respect to a horizontal plane. With such design, air contained in the first chamber (e.g., air bubbles ejected from the pipette) may more easily escape from said first chamber.

The first chamber (which, as mentioned above, may be the bottom chamber) may have a volume of 150 μL or less, preferably of 100 μL or less, and more preferably of 50 μL or less. The volume of the first chamber preferably is at least 5 μL, more preferably at least 14 μL. Furthermore, the first chamber may have a height of 20 mm or less, preferably 15 mm or less, more preferably 7.5 mm or less. Preferably, the height is at least 2 mm or at least 3 mm. The height of the first chamber preferably is ⅔ or less, or ½ or less of the device's total height. Preferably, the height of the first chamber is at least ⅙ or at least ¼ of the device's total height. The "total height" in this context may refer to the height of the combined space defined by the first and second chambers together.

The first chamber preferably provides a bottom area for growth ("growth area") of 35 mm² or less, preferably 15 mm² or less. The growth area of the first chamber preferably is at least 2.5 mm² or at least 7 mm².

The disturbance blocking structure may be integrally formed with at least one of the first sidewalls and/or with at least one of the second sidewalls. For example, the one or more first sidewalls may be contiguous with the one or more second sidewalls and the disturbance blocking structure may be molded in one piece with the first and second sidewalls.

The disturbance blocking structure may also be provided by a separate element. This element may be referred to as a "disturbance blocking element" or an "insert" in the context of the present disclosure.

The disturbance blocking element may be attached onto and/or inserted into a known cell incubation device (in particular, into/onto a known cell incubation well or into/onto a known multiwell plate). For example, the insert may be attached onto the sidewalls and/or inserted into a space formed by the sidewalls of such known device. The disturbance blocking element could thus easily be combined with standard wells and/or standard multiwell plates in order to provide wells and/or multiwell plates in accordance with the present invention. The disturbance blocking element could, for example, be clamped, welded and/or glued onto a known well or a known multiwell plate. Optionally, a seal or a sealing gasket could be provided between the first sidewalls and the disturbance blocking element.

The disturbance blocking element or insert may provide the second sidewalls and/or, for example when a multiwell plate is used, several second chambers and/or several disturbance blocking structures. The second sidewalls and/or the second chambers provided by the disturbance blocking element preferably coincide with the first chamber formed in the standard multiwell plate. Preferably, the disturbance blocking element or insert provides a plurality of first chambers (or even each first chamber) of the respective standard multiwell plate with a corresponding second chamber. The disturbance blocking structure could be formed integrally with the second sidewalls. Also in this case, a dark, light absorbing (e.g., black) material could be used for the disturbance blocking structure and/or the second sidewalls. This material may, for example, be polystyrene.

The cell incubation device (e.g., the well, the multiwell plate and/or the separate element) according to the invention may be provided in a sterile condition and/or may be sterilized.

According to a further aspect, the present invention relates to a method of incubating cells, in particular to a method of incubating non-adherent cells as a monolayer. The method may be a screening method for determining a response or a lack of response of diseased cells to therapeutic agents and/or cell mortality due to these therapeutic agents. As mentioned above, the cells preferably are one or several cells selected from the group consisting of: blood cells, bone marrow cells, dissociated lymph node tissue, and/or hematopoietic stem cells and may summarily be referred to as PBMCs in the context of the present disclosure.

The method according to the invention includes the steps of (a) providing a cell incubation device according to the invention, (b) introducing cells into the device.

The step of introducing cells into the device preferably includes introducing cells into the first chamber. Introducing cells into the first chamber may include inserting a tip of a pipette into the first chamber through the through hole. Preferably, the tip is inserted such that and/or the through hole is configured such that a pressure built-up in the first chamber is prevented. In this context, the tip of the pipette may be inserted through the second opening and/or through the open top of the device. The tip is thus preferably inserted through the second chamber and the through hole in order to inject cells into the first chamber. The cells preferably are delivered into the first chamber directly. Preferably, the cells are not injected into the second chamber. With most or all cells being provided in the first chamber, small cell populations may be sufficient for forming a monolayer on the inner bottom surface of the device that can be subjected to screening.

Preferably, less than 100,000 or less than 40,000 or less than 20,000 or less than 10,000 cells are added per device (in particular, per well) during the step of introducing cells into the first chamber. In other words, less than 20,000 or less than 10,000 cells may be added into the first chamber during the step of introducing cells therein.

Cell density may be, for example, less than 6000 cells per $mm^2$, less than 3000 cells per $mm^2$, less than 2000 cells per $mm^2$, or even less than 1000 cells per $mm^2$.

The method according to the invention preferably includes a further step of adding liquid to the device. The method according to the invention may thus include the steps of (a) providing a cell incubation device according to the invention, (b) introducing cells into the device, and (c) adding liquid to the device. The step of introducing cells into the device could also be referred to as "seeding".

The step of adding liquid to the cell incubation device preferably includes at least partially filling the second chamber with said liquid. Alternatively or additionally, it may also include at least partially wetting the disturbance blocking structure with the liquid. More preferably, liquid is added to the device until the disturbance blocking structure is at least partially or entirely submerged. In particular, the through hole may be at least partially or entirely submerged. The liquid may be added to the device after introducing the cells (which themselves may be suspended in a liquid) into the first chamber and preferably is layered on top of the cells. The liquid added to the device preferably is a medium. The medium may be, for example, RPMI, MEM, DMEM, IMEM and/or another medium known in the art.

The step of adding liquid to the device may include inserting a tip of a pipette into the second chamber through the second opening and/or through the open top of the device. In this context, the tip of the pipette preferably is arranged such that the liquid is not injected directly through the through hole. Preferably, the liquid is added to the second chamber by injecting the liquid towards and/or against the disturbance blocking structure and/or towards and/or against at least one of the second sidewalls. The liquid thus preferably flows through and/or partially fills the second chamber before reaching the first chamber. In other words, the liquid preferably is not directly injected into the first chamber, but rather reaches the first chamber indirectly. For example, the liquid (and substances contained therein) may reach the first chamber via slow flows and/or minor perturbations. Solutes contained in the liquid may also, for example, diffuse into the first chamber. Without wanting to be bound by theory, it is believed that this may reduce turbulences and/or currents in the first chamber.

The method according to the invention may further include the addition of one or several therapeutic agents to the cell incubation device. These may be added to the device in a separate step before and/or after introducing cells into the device. For example, one or several small molecule drugs may be added to the plates before adding cells (e.g., as a preliminary step), for example by transferring small droplets of drug in DMSO (e.g., at 1000× concentration) to the plate (e.g., by using an ECHO liquid handling system by Labcyte Inc., Sunnyvale, USA). Subsequently, the cells may be added to the wells, for example in a medium which then mixes with the drug(s). Alternatively or additionally, one or several therapeutic agents may be added to the cell incubation device during (for example, one or several therapeutic agents could be contained in liquid that is added in step (b)) and/or after introducing cells into the device. For example, one or several therapeutic agents may be added to the cell incubation device during and/or after the step of adding liquid (for example, one or several therapeutic agents could be contained in liquid that is added in step (c)). Exemplary therapeutic agents that may be added after introducing cells into the device may include small molecules, biologics or cell based therapeutics. The method according to the invention may thus include the steps of (a) providing a cell incubation device according to the invention, (b) introducing cells into the device, (c) adding liquid to the device, and (d) adding one or more therapeutic agent(s) to the device. Step (d) of adding one or more therapeutic agent(s) to the device may be performed before step (b), during step (b), during step (c) and/or after step (c).

The therapeutic agent(s) is/are preferably added to the cell incubation device in a manner that reduces currents and/or turbulences in the first chamber. For example, the therapeutic agent(s) may be added to the second chamber in a concentration that is higher than the target concentration in the device and may then diffuse through the through hole and/or through the membrane of the disturbance blocking structure into the first chamber. Alternatively or additionally, the therapeutic agent(s) may be injected into the second chamber such that the flow is directed towards and/or against the disturbance blocking structure and/or towards and/or against at least one of the second sidewalls, as described above for the step of adding liquid (e.g., medium) to the device.

The method according to the invention may further include a step of incubating the cells for a certain period of time. The method according to the invention may thus include the steps of (a) providing a cell incubation device according to the invention, (b) introducing cells into the device, (c) adding liquid to the device, (d) adding one or more therapeutic agent(s) to the device (wherein these therapeutic agents could be added before step (b), could be contained in liquid added in steps (b) and/or (c), and/or could be added in a separate step after steps (b) and/or (c)), and (e) incubating the cells for a certain period of time. Incubation preferably is performed such that the non-adherent cells form a monolayer, preferably on the inner bottom surface of the device (i.e., preferably on the inner surface of the bottom wall).

The incubation time may be selected such that an effect of the one or several therapeutic agents on the cell population becomes apparent. The cells may be incubated, for example, at 37° C. in a $CO_2$ incubator with 5% $CO_2$. The duration of the incubation step of the methods of the invention is not particularly limited.

However, since isolated non-adherent cells of the types mentioned above may represent a fragile cell population that is difficult to maintain over extended periods of time, incubation times of less than 48 hours or 36 hours are preferred. The incubation time may be 1 to 24 hours (e.g., overnight), less than 12 hours, or even less than 1 hour.

The step of providing a cell incubation device may include providing a multiwell plate with multiple wells according to the invention (e.g., with more than 10, more than 20, more than 90, more than 250, or more than 1000 wells according to the invention). Thereby, the screening may be performed for multiple therapeutic agents simultaneously. For example, cells may be incubated with different active substances, different active substance combinations and/or different active substance concentrations in different wells of the multiwell plate.

The method according to the invention may further include a step of fixating the cells. The method according to the invention may thus include the steps of (a) providing a cell incubation device according to the invention, (b) introducing cells into the device, (c) adding liquid to the device, (d) adding one or more therapeutic agent(s) to the device (wherein these therapeutic agents could be added before step (b), could be contained in liquid added in steps (b) and/or (c), and/or could be added in a separate step after steps (b) and/or (c)), (e) incubating the cells for a certain period of time, and (f) fixating the cells.

The step of fixating the cells may include the addition of one or more fixatives to the second chamber. The fixative(s) is/are preferably added to the device in a manner that reduces currents and/or turbulences in the first chamber. For example, the fixative(s) may be added to the second chamber in a concentration that is higher than the target concentration in the device and may then flow and/or diffuse through the through hole, through the membrane and/or through the foam of the disturbance blocking structure into the first chamber. Alternatively or additionally, the fixative(s) may be injected into the second chamber such that the flow is directed towards and/or against the disturbance blocking structure and/or towards and/or against at least one of the second sidewalls, as described above for the step of adding liquid to the device.

The cells can be fixated on the inner bottom surface of the first chamber by using known fixatives, for example formaldehyde. Fixating is normally performed immediately prior to an addition of means for visualizing the cells, cell components, and/or cellular proteins. If desired, a detergent can be added for cell permeabilization, for example Triton X-114. Fixing the cells may increase stability of the monolayers for subsequent analysis.

The method according to the invention may further include a step of staining the cells. The method according to the invention may thus include the steps of (a) providing a cell incubation device according to the invention, (b) introducing cells into the device, (c) adding liquid to the device, (d) adding one or more therapeutic agent(s) to the device (wherein these therapeutic agents could be added before step (b), could be contained in liquid added in steps (b) and/or (c), and/or could be added in a separate step after steps (b) and/or (c)), (e) incubating the cells for a certain period of time, and (g) staining the cells. In addition, also the step (f) of fixating the cells described above may be included.

Preferably, the step of staining the cells is performed after fixation. The step may include the addition of one or more dyes to the second chamber. The dye(s) is/are preferably added to the cell incubation device in a manner that avoids or reduces currents and/or turbulences in the first chamber. For example, the dye(s) may be added to the second chamber in a concentration that is higher than the target concentration in the device and may then flow and/or diffuse through the through hole, through the membrane, and/or through the foam of the disturbance blocking structure into the first chamber. Alternatively or additionally, the dye(s) may be injected into the second chamber such that the flow is directed towards and/or against the disturbance blocking structure and/or towards and/or against at least one of the second sidewalls, as described above for the step of adding liquid to the device.

The step of staining the cells may also include a partial removal of supernatant before addition of the dye(s). By removing the supernatant from the second chamber and preferably pointing the tip of the pipette towards the disturbance blocking structure and/or towards one of the second sidewalls, currents and/or turbulences in the first chamber may be avoided or reduced also during this step.

Suitable dyes are disclosed in "*Molecular Probes Handbook, A Guide to Fluorescent Probes and Labeling Technologies*". As a non-limiting example, the viability dye may be added in a 1:1000 mix dissolved in isotonic solution, e.g. PBS. In this regard, Invitrogen live/dead fixable 488 dye is particularly useful. The dye may be a viability dye indicating whether the cells forming the monolayer are viable. The method according to the invention may also include a step of intracellular and/or extracellular antibody staining.

The method according to the invention may further include a step of taking images of the cells in the device. The method according to the invention may thus include the steps of (a) providing a cell incubation device according to the invention, (b) introducing cells into the device, (c) adding liquid to the device, (d) adding one or more therapeutic agent(s) to the device (wherein these therapeutic agents could be added before step (b), could be contained in liquid added in steps (b) and/or (c), and/or could be added in a separate step after steps (b) and/or (c)), (e) incubating the cells for a certain period of time, and (h) taking images of the cells in the device. In addition, also the above-mentioned steps (f) of fixating the cells and (g) of staining the cells may be included in the method, preferably before taking images of the cells. When a multiwell plate is used, the cells (in particular, the monolayers formed during incubation) may preferably be imaged directly in the multiwell plate.

The cells may be imaged according to any methods known in the art and/or described herein. The step of imaging the cells may comprise imaging both stained and non-stained components and/or may comprise imaging under conditions in which the stain is visible or is not visible (e.g., imaging in bright-field (wherein a fluorescent stain would not be visible) and fluorescent microscopy (wherein a fluorescent stain would be visible), or combinations thereof. Preferably, confocal microscopy is used to image the cells. The Opera Phenix High Content Screening confocal microscope by Perkin Elmer of Waltham, Mass., USA may be employed for this purpose.

The method according to the invention may further include a step of performing image analysis on the images taken of the cells. The method according to the invention may thus include the steps of (a) providing a cell incubation device according to the invention, (b) introducing cells into the device, (c) adding liquid to the device, (d) adding one or more therapeutic agent(s) to the device (wherein these therapeutic agents could also be contained already in liquid added in steps (b) and/or (c)), (e) incubating the cells for a certain period of time, (h) taking images of the cells in the device, and (i) performing image analysis on the images taken of the cells. In addition, also the above-mentioned steps (f) of fixating the cells and (g) of staining the cells may be included in the method, preferably before taking images of the cells.

The step of performing image analysis preferably provides a feedback that indicates a response or lack of response of diseased cells in the population to the therapeutic agent(s). In particular a feedback indicating cell mortality of diseased cells within the population may be provided. Alternatively or additionally, the step of performing image analysis may include providing a feedback that indicates a response or lack of response of healthy cells in the population to the therapeutic agent(s), in particular a feedback indicating the mortality of healthy cells by exposure to the therapeutic agent(s). Alternatively or additionally, the step of performing image analysis may include determining interaction propensities between different cell types as measured using an interaction score and method as disclosed in EP application number 17 15 7806.5 (incorporated herein by reference). Diseased and healthy cells may be distinguished by means of, for example, a fluorescent dye or fluorescently labeled antibody used to stain the cells before or after fixation.

By providing an indication of both, the a response or lack of response of diseased cells and the a response or lack of response of healthy cells, the step of performing image analysis may provide one, two or more rankings that indicate which of the therapeutic agent(s) (i.e. which of the therapeutic agents, which of the therapeutic agent concentrations, and/or which of the therapeutic agent combinations tested) are most effective against a patient's disease and least harmful to the patient's healthy cells.

The method according to the invention may further include a step of providing an output that indicates preferred treatment options for the patient's disease (e.g., to a physician). In particular, the differential effect that the drug has on healthy cells compared to diseased cells may be used as a predictor of clinical outcome.

According to a further aspect, the invention relates to the use of a multiwell imaging plate in accordance with the foregoing description for drug screening and/or chemosensitivity testing. Drug screening and/or chemosensitivity testing may involve incubating monolayers of non-adherent cells in accordance with the method described above.

Robotic or other automated aspirators (e.g., pipetting systems) may be employed in all steps of the method involving the use of a pipette.

The invention will be described in more detail with reference to the figures below. These figures disclose embodiments of the invention for illustrational purposes only. In particular, the disclosure provided by the figures is not meant to limit the scope of protection conferred by the invention.

FIG. 1A a schematic cross sectional side view of a prior art well illustrating microcurrents in the well;

FIG. 1B a further schematic cross sectional side view of the well shown in FIG. 1A illustrating pipetting in the well;

FIG. 1C a schematic top view of the well shown in FIGS. 1A and 1B that schematically illustrates a cell distribution in the well after incubation;

FIG. 2A a schematic cross sectional side view of a well in accordance with a preferred first embodiment of the present invention;

FIG. 2B a further schematic cross sectional side view of the well shown in FIG. 2A illustrating pipetting in the well;

FIG. 2C a further schematic cross sectional side view of the well shown in FIGS. 2A and 2B illustrating the well's dimensions;

FIG. 2D a schematic top view of the well shown in FIGS. 2A, 2B, and 2C that illustrates a cell distribution in the well after incubation;

FIG. 3 a schematic cross sectional side view of a well in accordance with a variation of the embodiment shown in FIGS. 2A to 2D;

FIG. 4 a schematic cross sectional side view of a well in accordance with a further variation of the embodiment shown in FIGS. 2A to 2D;

FIG. 5 a perspective view of a disturbance blocking element for a known multiwell plate (not shown) in accordance with the principle illustrated in FIG. 4;

FIG. 6 a schematic cross sectional side view of a well in accordance with a further variation of the embodiment shown in FIGS. 2A to 2D;

FIG. 7 a schematic cross sectional side view of a well in accordance with a further embodiment of the invention;

FIG. 8 a schematic cross sectional side view of a well in accordance with a further embodiment of the invention;

FIG. 9 a schematic cross sectional side view of a well in accordance with a further embodiment of the invention;

FIG. 10 a schematic top view, cross sectional side views and a perspective view of a multiwell plate with an integrally formed disturbance blocking structure, in accordance with the invention;

FIG. 11 time lapse images taken during addition of liquid to a commercially available 384-well high content imaging plate and the second chamber of a cell culture device according to FIG. 10.

FIGS. 1A to 1C schematically illustrate a well 1 of a multiwell plate known from the prior art. As shown in FIG. 1A, the well 1 and has sidewalls 3 and a bottom 5 that is opposite an open top end 7 of the well 1.

The sidewalls 3 define a chamber 10 into which a liquid (e.g., a buffer medium) containing non-adherent cells 15 is introduced through the open top end 7. The cells 15 are then incubated for a certain period of time in the well 1. As disclosed in co-pending WO 2016/046346, the well 1 may be used to incubate the cells 15 as a monolayer, which can then be fixated and imaged.

As mentioned above, it has been discovered by the present inventors that the cells 15, despite being non-adherent, may tend to cluster close to the sidewalls 3 of the well 1 in some instances. This effect is shown (in a schematic and exaggerated manner) in FIG. 1C.

Without wanting to be bound by theory, it is believed that this effect may, at least in part, result from currents $C_1$ occurring in the well 1 during handling and/or incubation. Without wanting to be bound by theory, it is believed that these currents $C_1$ may, at least in part, result from non-uniform evaporation and/or non-uniform convection at the well's open end 7, as schematically illustrated in FIG. 1A. With the upper surface of the liquid 10 forming a meniscus 12, it is believed (still without wanting to be bound by theory) that evaporation and/or convection $E_s$ proximate to the sidewalls 3 may be stronger than evaporation and/or convection $E_c$ in the center region of the well 1.

Furthermore, again without wanting to be bound by theory, it is believed that the effect observed by the inventors may, at least in part, result from currents $C_2$ that are introduced when pipetting. These currents $C_2$ are schematically illustrated in FIG. 1B, where also a tip 20 of a pipette is shown.

Without wanting to be bound by theory, it is further believed that another factor that may be contributing to the effect observed by the inventors (most likely to a smaller extent) could be the fact that the sidewalls 3 of many known wells 1 extend at an angle α with respect to the bottom wall 5 (which may be an angle measured between the inner bottom surface of the bottom wall 5 and the inner surface of the sidewalls 3) that is larger than 90°. Known multiwell plates thus often have a conical design with the sidewalls of the wells tapering towards the bottom.

FIGS. 2A to 2D show a cell incubation device according to the invention, more specifically, a well 100 of a multiwell plate (not shown). The well 100 comprises first sidewalls 103 and a bottom wall 105 that define a first, bottom chamber 111 and second sidewalls 104 that define a second, top chamber 112. The second chamber 112 may be arranged above and/or on top of the first chamber 111 and may have an open top end 107. The open top end preferably is large enough to introduce the tip 20 of a pipette into the second chamber 112. The bottom wall 105 preferably is transparent.

As shown for this illustrative embodiment, the first sidewalls 103 and the second sidewalls 104 may optionally be contiguous and integrally formed with each other. They may, in fact, be formed by a single continuous wall. As discussed in more detail below, the first and second sidewalls 103, 104 may, however, also be provided as separate pieces and/or separate elements that are attached to each other in order to form the cell incubation device of the invention.

As further shown in FIGS. 2A to 2D, the well 100 may include a disturbance blocking structure that preferably is provided by an intermediate floor 121. The intermediate floor 121 may be provided with a through hole 123 that provides a liquid connection between the first and second chambers 111, 112. The first chamber 111 may be filled with a liquid containing non-adherent cells 15 that forms a meniscus 12. The liquid may be injected into the first chamber 111 through the through hole 123, for example, by extending a pipette through said through hole 123.

As mentioned above, the through hole 123 preferably is configured to prevent a pressure built-up when injecting cells 15 through the through hole 123 into the first chamber 111. This may be achieved, for example, by providing the trough hole 123 with a width W or a diameter D of at least 0.5 mm, at least 0.8 mm or at least 1 mm. Alternatively or additionally, the through hole 123 could be provided with a non-circular and/or irregular shape for ensuring that the tip 20 of the pipette does not entirely fill the through hole 123 when it is inserted. Furthermore, alternatively or additionally, the intermediate floor 121 could be provided with additional vent holes (not shown).

Preferably, sufficient liquid(s) is/are filled into the well 100 to at least partially or fully submerge the disturbance blocking structure 121. In other words, sufficient liquid(s) is/are added to the well 100 to at least partially fill the second chamber 112.

As illustrated in a very schematic and exaggerated manner in the top view of FIG. 2D (where the intermediate floor 121 illustrated by cross-hatching), it has been found by the inventors that incubation in the well 100 may provide monolayers of non-adherent cells 15 exhibiting a reduced tendency of cell accumulation along the sidewalls 103 of the first chamber 111 and, therefore, a more homogeneous distribution of cells 15 across the inner surface of the bottom wall 105. Without wanting to be bound by theory, it is believed that this effect may be achieved, at least in part, by restricting the currents $C_1$ that result from non-uniform evaporation and/or non-uniform convection at the meniscus 12 in the region of the well's open top end 107 at least to some extent to the second, top chamber 112 (see FIG. 2A). Moreover, again without wanting to be bound by theory, it is believed that the effect observed may be achieved, at least in part, by restricting the currents $C_2$ caused by insertion of the pipette's tip 20 and/or aspiration of liquid into and/or ejection of liquid from the tip 20 during pipetting at least to some extent to the second chamber 112 (see FIG. 2B). This may be achieved, in particular, by aspirating liquid into and/or ejecting liquid from the tip 20 while the tip 20 is pointing towards and/or resting on the intermediate floor 121 and/or the second sidewalls 104. It is thus believed, again without wanting to be bound by theory, that the intermediate floor according to the invention avoids currents from reaching the first chamber 111 or at least reduces these currents. The disturbance blocking structure according to the invention may thus prevent or reduce disturbances that could adversely affect monolayer formation.

In addition, an angle β formed between the first sidewalls 103 and the bottom wall 105 (which may be an angle measured between the inner bottom surface of the bottom wall 105 and the inner surface of the sidewalls 103) optionally may be approximately 90° or smaller. The first sidewalls 103 of the well 100 may thus be arranged and/or shaped such that they do not taper towards the bottom 105 of the well. They may even taper towards the top 107 of the well 100. While it has been found that adequate results may also be achieved when this is not the case (and the angle β may thus also be larger than 90°, it is believed, again without wanting to be bound by theory, that such design may contribute further to reducing cell agglomeration in the region of the first sidewalls 103.

FIG. 2C schematically illustrates the volume $V_1$ of the first chamber 111 and the volume $V_2$ of the second chamber 112. As described above, the first chamber 111 preferably has a volume $V_1$ of 150 μL or less, more preferably of 100 μL or less, and even more preferably of 50 μL or less. However, the volume $V_1$ of the first chamber preferably is at least 5 μL and more preferably at least 14 μL. The volume $V_2$ of the second chamber is preferably is at least 10 μL, more preferably at least 20 μL, and even more preferably at least 40 μL. Preferably, the volume $V_2$ of the second chamber is 300 μL or less, more preferably 70 μL or less.

FIG. 2C further illustrates the height $H_1$ of the first chamber 111 and the total height $H_2$ of the well 100 (which corresponds to the combined height of the first chamber 111 and the second chamber 112 in the illustrative embodiment of FIG. 2C). As also described above, the first chamber 111 may have a height $H_1$ of 20 mm or less, preferably 15 mm or less, more preferably 7.5 mm or less. Preferably, the height $H_1$ is at least 2 mm or at least 3 mm. The height $H_1$ of the first chamber 111 preferably is ⅔ or less, or ½ or less of the device's total height $H_2$. Preferably, the height $H_1$ of the first chamber 111 is at least ⅙ or at least ¼ of the device's total height $H_2$.

FIG. 3 shows a well 100 in accordance with a variation of the embodiment shown in FIGS. 2A to 2D. In the well 100 of FIG. 3, a disturbance blocking structure in the form of an intermediate floor 121 is provided by a separate disturbance blocking element or insert 120 (illustrated by a dotted line in FIG. 3) that is inserted into a space formed by the first sidewalls 103. The intermediate floor 121 may thus be arranged in the space formed by the first sidewalls 103.

The disturbance blocking structure 120 of FIG. 3 may form the second chamber 112 and/or provide the second sidewalls 104. The intermediate floor could be integrally formed with the second sidewalls 104 in this case or as a separate element which is attached thereto (e.g., by gluing and/or welding).

The disturbance blocking structure 120 of FIG. 3 could be clamped onto and/or attached (e.g., by gluing and/or welding) to a structure (not shown) forming one or more first chambers 103 (e.g., to the sidewalls 103 shown in FIG. 3). Such structure could be, for example, a known, existing (e.g., standard) multiwell plate. In particular, such structure could be a known multiwell imaging plate.

FIGS. 4 and 5 show a well 100 according to a further variation of the embodiment shown in FIGS. 2A to 2D. As will be appreciated by the skilled person, also this variation uses a separate disturbance blocking element 120. Also in this case, the disturbance blocking element 120 includes a disturbance blocking structure in the form of an intermediate floor 121, which may be arranged on or above the first sidewalls 103. Again the disturbance blocking element 120 may provide the second chamber 112 and/or the second sidewalls 104. The intermediate floor 121 could be integrally formed with the second sidewalls 104 or as a separate element which is attached thereto (e.g., by gluing and/or welding).

Also the disturbance blocking structure 120 of FIG. 4 could be clamped onto or attached (e.g., by gluing and/or welding) to a structure (not shown) forming one or more first chambers 103 (e.g., to the sidewalls 103 shown in FIG. 4). Such structure could be, for example, a known, existing (e.g., standard) multiwell plate. In particular, such structure could be a known multiwell imaging plate.

FIG. 5 illustrates in more detail a preferred design of the disturbance blocking element 120 in accordance with the principle illustrated in FIG. 4. As shown in FIG. 5, the disturbance blocking element 120 may provide multiple second chambers 112 that may be located such that they are disposed above the wells of a known multiwell plate when the disturbance blocking element 120 is positioned thereon.

Although it is not shown in FIGS. 4 and 5, it is noted that the disturbance blocking element 120 according to this variation may also include protrusions that protrude into the space formed by the first sidewalls 103. Such protrusions may, for example, assist a user in assembling the cell incubation device correctly by defining the arrangement of the disturbance blocking element 120 with respect to the wells of the known multiwell plate.

As will be apparent to the skilled person, a seal or a sealing gasket (not shown) could be provided between the first sidewalls 103 and the disturbance blocking element 120 in the variations according to FIGS. 3, 4 and 5.

The intermediate floor 121 may be substantially horizontal and/or substantially parallel to the bottom surface 105 (see FIGS. 2A, 2B, 2C, 3 and 4). The intermediate floor 121 may also be substantially perpendicularly to the first sidewalls 103 and/or to the second sidewalls 104.

The intermediate floor 121, however, may also extend upwardly from the location at which it connects to the first sidewalls 103 and or to the second sidewalls 104.

For example, as schematically illustrated in FIG. 6, the intermediate floor 121 may extend upwardly from the sidewalls towards the through hole 123. In this case, an angle α between the second sidewalls 104 and the intermediate floor 121 in a vertical cross section of the device preferably is at least 70°, at least 80°, at least 85°, or at least 87°. The intermediate floor may thus extend upwardly at an angle δ of less than 20°, less than 10°, less than 5°, or less than 3° with respect to a horizontal plane P. The variation according to FIG. 6 may be implemented in any of the embodiments according to FIGS. 2A to 5.

FIG. 7 shows a schematic cross sectional side view of a well 200 in accordance with a further embodiment of the invention. In this case, the first chamber 211 and the second chamber 212 are laterally adjacent with respect to each other. As shown, a disturbance blocking structure 221 may extend in a substantially vertical direction with a through hole 223 being provided therein. Also in this case, the disturbance blocking structure may reduce or avoid disturbing the formation of a monolayer of cells 15 in the first chamber 211 when liquids are added to and/or aspirated from the second chamber 212.

FIGS. 8 and 9 show embodiments wherein a disturbance blocking structure is provided by a membrane 321, 421, respectively.

In FIG. 8, the membrane 321 extends between a first, bottom chamber 311 and a second, top chamber 312 that is arranged on top or above of the first chamber 311. The membrane may, on the one hand, avoid or reduce disturbances in the second chamber 312 from reaching the first chamber 311 (e.g., by making the membrane tense). On the other hand, the membrane 321 may be permeable to certain fluids and/or it may allow the diffusion of certain substances, thus allowing fluids and/or substances added to the second chamber 321 to reach the first chamber 311. The membrane 321 may thus not have to be provided with a through hole for inserting a pipette. The membrane could, for example, be placed onto the first chamber after introducing the cells 15 therein. The second chamber 321 could then be formed by a separate element mounted on top of the first chamber 311, similarly to the manner described with reference to FIGS. 4 and 5 above. The membrane 321, however, could also be provided with a through hole or cut for inserting a pipette tip therethrough.

In FIG. 9, the first chamber 411 and the second chamber 412 are arranged side-by-side. The membrane 421 may be arranged vertically, but may otherwise be similar to the membrane 321 described with reference to FIG. 8 above.

Figure 1A:
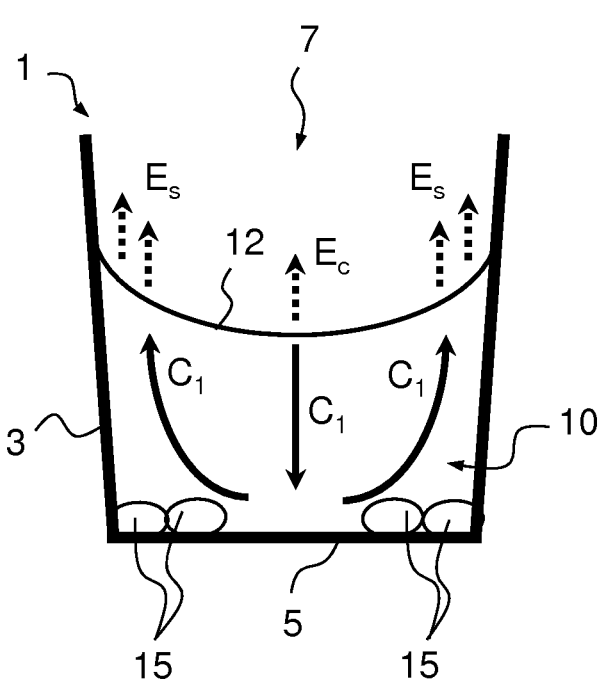
Figure 1B:
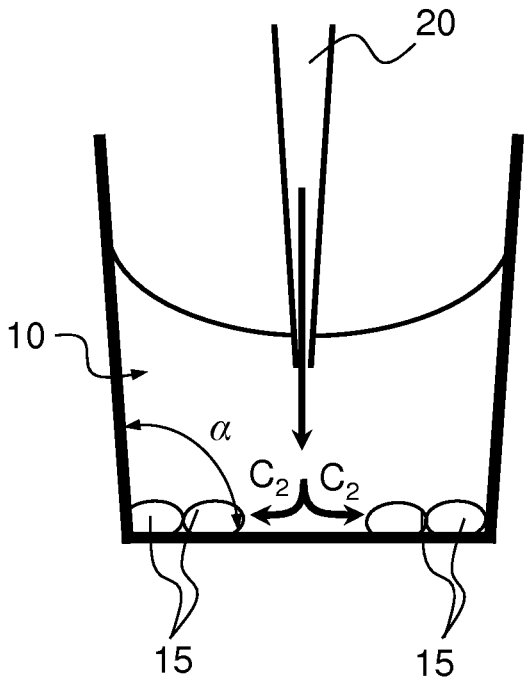
Figure 1C:
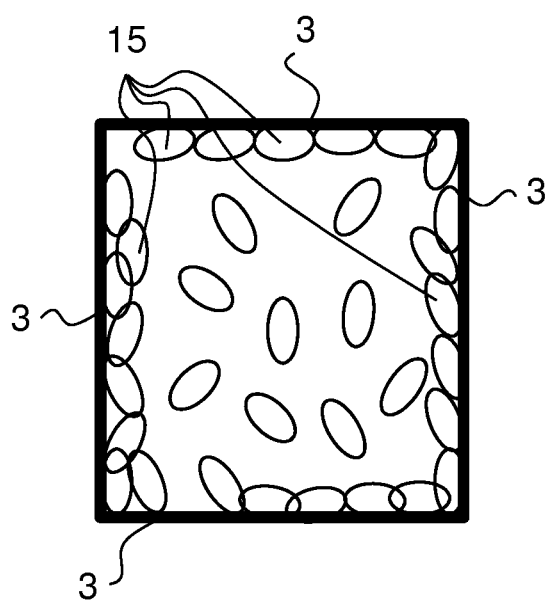
Figure 2A:
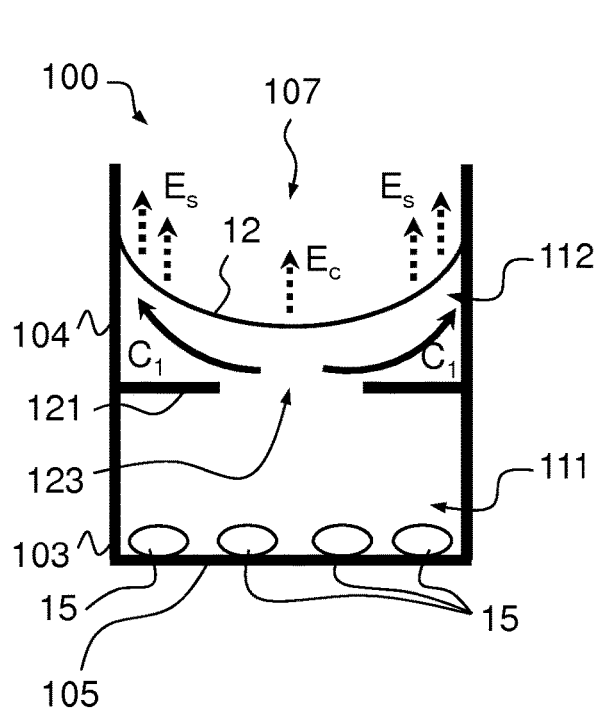
Figure 2B:
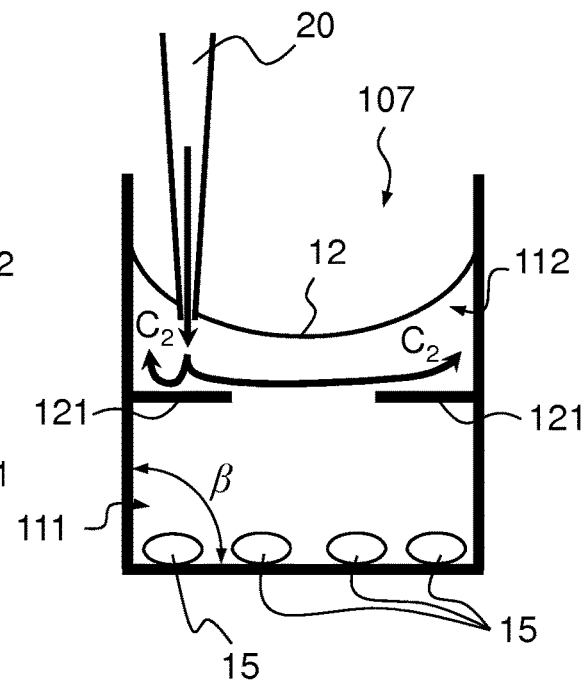
Figure 2C:
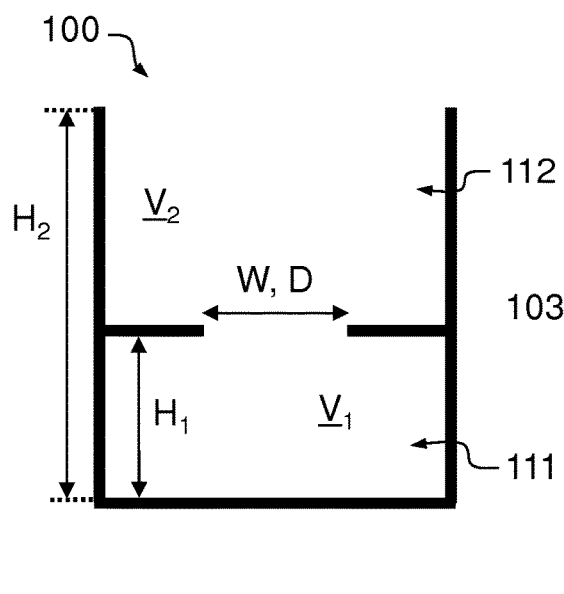
Figure 2D:
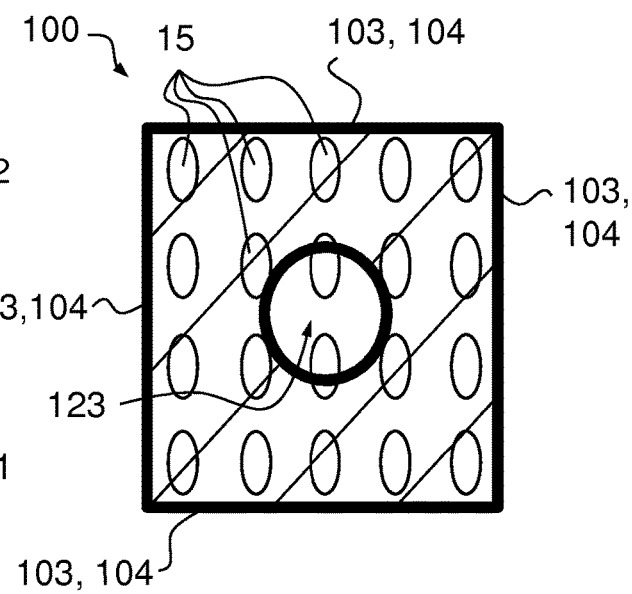
Figure 6:
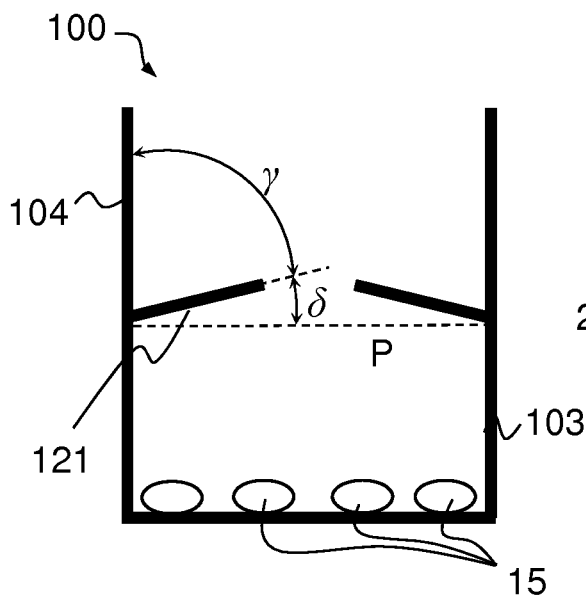
Figure 7:
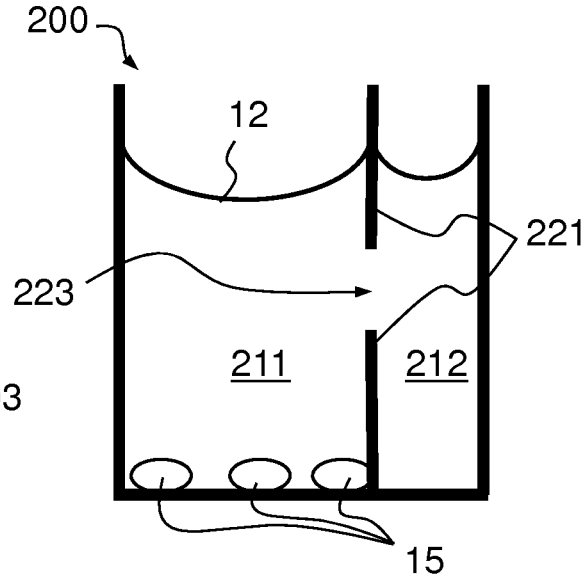
Figure 8:
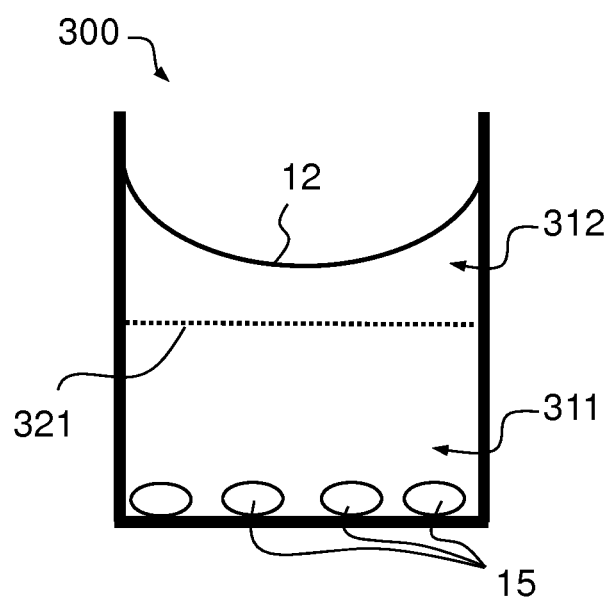
Figure 9:
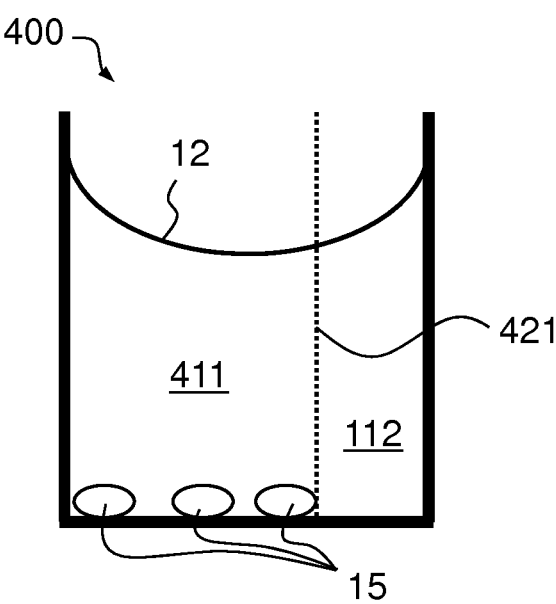
Figure 10:
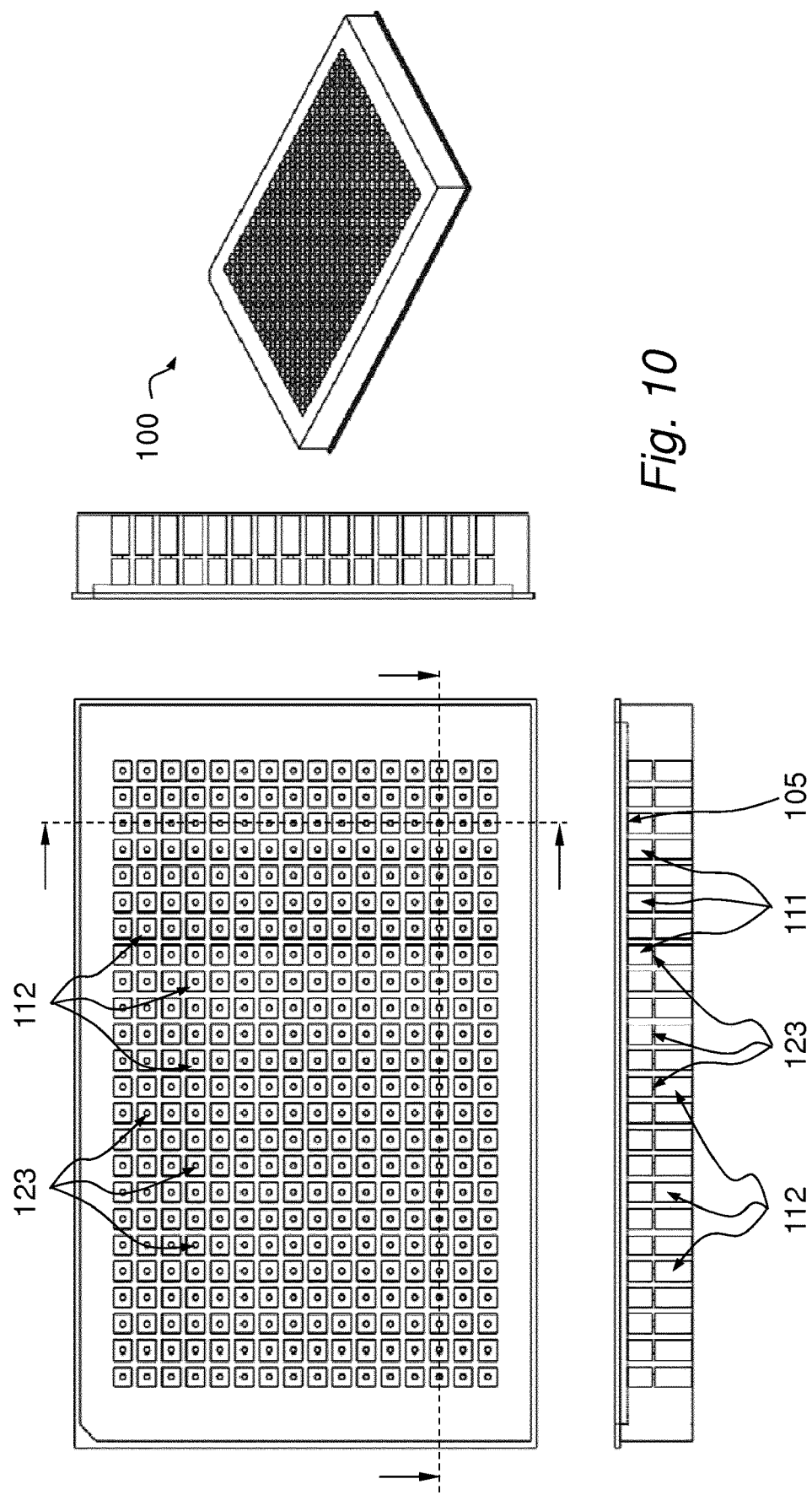
FIG. 10 shows a schematic top view, cross sectional side views and a perspective view of a multiwell plate with an integrally formed disturbance blocking structure according to the invention.

$2 \times 10^7$ primary human PBMCs were stained with Hoechst 33342 (1:1000 for 15 minutes at 37° C.) for consecutive live cell imaging, spun down and re-suspended in RPMI (with 10% FBS, penicillin, and streptomycin being added) to a concentration of $4 \times 10^5$ cells. 50 µl of the cell suspension were then transferred into (a) a Perkin Elmer "Cell Carrier" 384 well standard screening plate, and (b) the exemplary cell culture device according to the invention, in each case by using an Eppendorf Xplorer 12-channel motorized pipette. In the cell culture device according to the invention, the total well depth $H_2$ according to FIG. 2C was 11.5 mm and the disturbance blocking structure 121 was mounted at a distance $H_1$ of 5.5 mm above the well bottom 105. The through hole 123 was centered inside the well as viewed from the top and had a hexagonal cross section with a side length of 1 mm and a width W of 2.5 mm.

Cells were incubated for 24 hours and formed a monolayer of approximately $2\times10^4$ cells on the bottom of each well. After incubation, plates were transferred to a fluorescent microscope and imaged immediately. Live cell imaging was done with a Leica AF 6000 microscope equipped with a Leica N PLAN 10.0×0.25 DRY objective and a DFC360FX camera. Live cell imaging movies were taken at maximal light power, 12 bit resolution, an exposure time of 20 milliseconds and a gain of 6 at maximal frame rate. Whilst live cell images were being recorded, 15 μL of 0.5% formaldehyde and 0.1% Triton X114 in PBS were added with an automatic pipette to each culture device (i.e. to the Perkin Elmer "Cell Carrier" 384 well standard screening plate and the exemplary cell culture device according to the invention). The images of FIG. 11 each show a representative portion of the respective well (approximately ¼ of the well's total surface).

Figure 11:
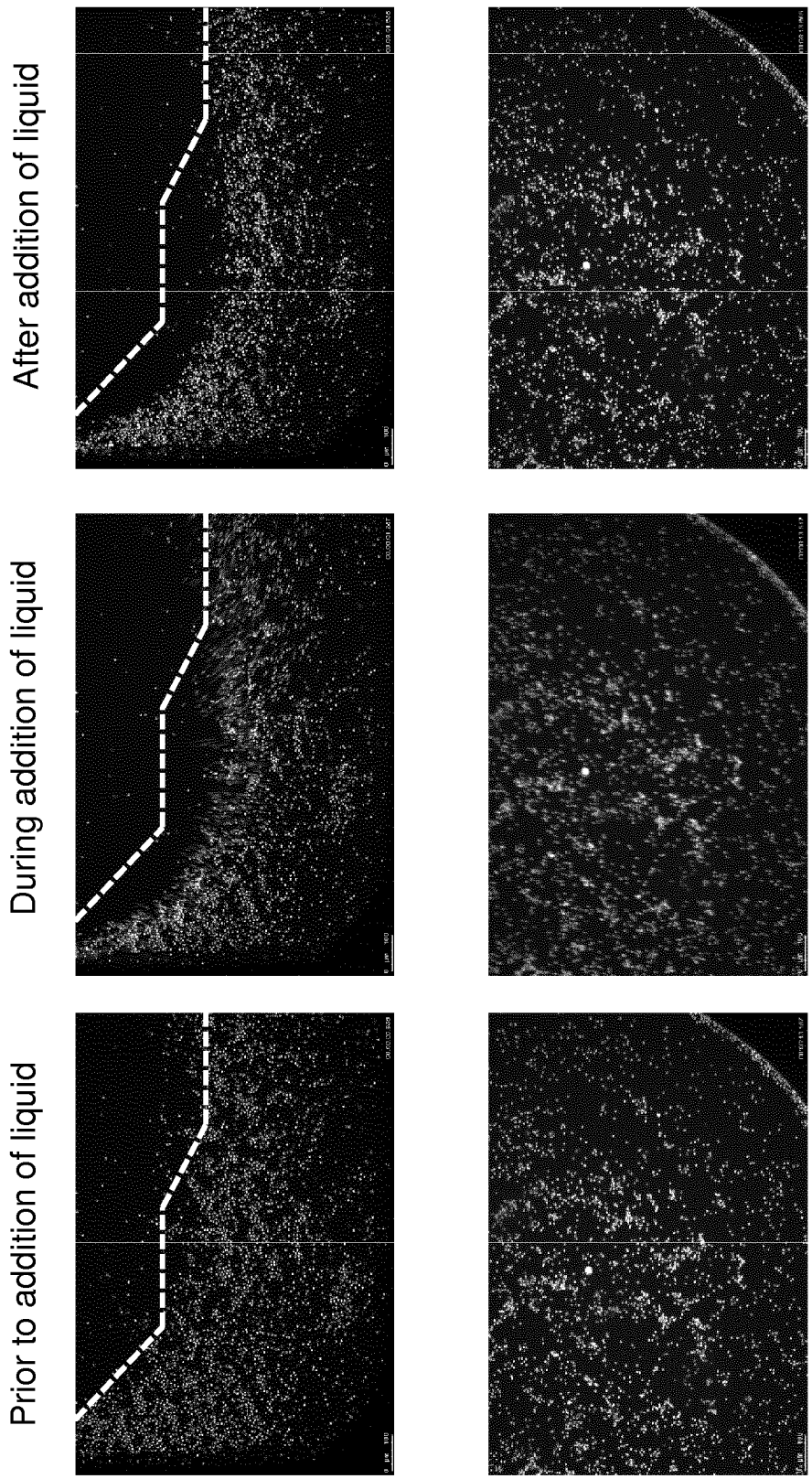
FIG. 11 shows time lapse images taken during addition of liquid to a commercially available 384-well high content imaging plate (top) and the second chamber of a cell culture device according to the invention (bottom). The cell culture device used in this illustrative example corresponds to a well of the multiwell plate shown in FIG. 10.

The images prior to and post pipetting shown in FIG. 11 indicate that the cell monolayers are more evenly formed during incubation over the entire surface in the culture device according to the present invention (bottom left image) when compared to the Perkin Elmer "Cell Carrier" 384 well standard screening plate (top left image). As apparent from the top left image shown in FIG. 11, only few cells have settled in the central portion of the Perkin Elmer well. Moreover, the cell distribution in the device according to the invention remains substantially unchanged upon addition of liquid to the second chamber (bottom right image). In comparison, the addition of liquid to the prior art Perkin Elmer "Cell Carrier" 384 well standard screening plate has a much more significant effect (top right image).

In view of the above, the present invention provides cell incubation devices, in particular cell incubation wells and multiwell plates, that achieve a more even formation of monolayers by preventing or reducing disturbances from acting on the cells during formation of the monolayers. Furthermore, screenings may be performed on relatively small cell populations since more cells of the population can accurately be identified during image analysis.

While aspects of the invention are illustrated and described in detail in the figures and in the foregoing description, such illustration and description is to be considered illustrative or exemplary and not restrictive. Also reference signs in the claims should not be construed as limiting the scope.

It will also be understood that changes and modifications may be made by those of ordinary skill within the scope and spirit of the following claims. In particular, the present invention covers further embodiments with any combination of features from different embodiments described above. It is also to be noted in this context that the invention covers all further features shown in the figures individually, although they may not have been described in the previous or following description. Also, single alternatives of the embodiments described in the figures and the description and single alternatives of features thereof can be disclaimed from the subject matter according to aspects of the invention.

Whenever the word "comprising" is used in the claims, it should not be construed to exclude other elements or steps. Similarly, the indefinite article "a" or "an" does not exclude a plurality. A single unit may fulfill the functions of several features recited in the claims. It should also be understood that the terms "essentially", "substantially", "about", "approximately" and the like used in connection with an attribute or a value may define the attribute or the value in an exact manner in the context of the present disclosure. The terms "essentially", "substantially", "about", "approximately" and the like could thus also be omitted when referring to the respective attribute or value.

The Invention may Inter Alia Relate to the Following Aspects:

1. Multiwell imaging plate for incubating monolayers of non-adherent cells (15), the plate including multiple wells, wherein at least some of the wells comprise:
   a first chamber (111), the first chamber (111) being formed by one or more first sidewalls (103) and a bottom wall (105);
   a second chamber (112), the second chamber (112) being formed by one or more second sidewalls (104) and including an opening (107) for introducing liquids, wherein the second chamber (112) is arranged on top of the first chamber (111);
   a disturbance blocking structure provided between the first chamber (111) and the second chamber (112), wherein the disturbance blocking structure preferably is provided by an intermediate floor (121);
   wherein the disturbance blocking structure preferably is provided with at least one through hole (123) that provides a liquid connection between the first and second chambers (111, 112), wherein the at least one through hole (123) preferably is provided in and/or through the intermediate floor (121);
   wherein the through hole (123) preferably is configured for a tip of a pipette being inserted through the second chamber into the first chamber through said through hole (123).
2. Multiwell plate according to aspect 1, wherein, in a top view of the respective well, the through hole (123) is spaced from the first and/or second sidewalls (103, 104).
3. Multiwell plate according to aspect 1 or 2, wherein, in a top view of the respective well, the through hole (123) is formed substantially in the center of the well.
4. Multiwell plate according to any of the preceding aspects, wherein the one or more first sidewalls (103) are made of a dark, light absorbing material and/or the bottom wall (105) is transparent.
5. Multiwell plate according to any of the preceding aspects, wherein the intermediate floor (121) protrudes into the respective well (100) along at least a portion of the wells' periphery.
6. Multiwell plate according to any of the preceding aspects, wherein the intermediate floor (121) extends in a substantially horizontal plane.
7. Multiwell plate according to any of the preceding aspects, wherein the intermediate floor (121) is solid and/or self-supporting.
8. Multiwell plate according to any of the preceding aspects, wherein an inner bottom surface of the bottom wall (105) is substantially flat and/or not microstructured.
9. Multiwell plate according to any of the preceding aspects, wherein the through hole (123) is wider than 1 mm and/or has a diameter of at least 1 mm.
10. Multiwell plate according to any of the preceding aspects, wherein the first chamber (111) has a volume of 150 μL or less, preferably of 100 μL or less, and more preferably of 50 μL or less.
11. Multiwell plate according to any of the preceding aspects, wherein the one or more first sidewalls (103) and the one or more second sidewalls (104) are contiguous with each other and the disturbance blocking structure is formed integrally with said first and second sidewalls (103, 104).

12. Multiwell plate according to any of the preceding aspects, wherein the intermediate floor (121) is connected to the first sidewalls (103) along at least a portion of its periphery.
13. Multiwell plate according to any of aspects 1 to 10, wherein the disturbance blocking structure is provided by a disturbance blocking element (120) that is inserted into and/or attached onto a structure forming a plurality of first chambers (103).
14. Method of incubating monolayers of non-adherent cells (15), the method including the following steps:
providing a multiwell plate according to any of aspects 1 to 13;
introducing non-adherent cells (15) into at least some of the wells;
adding liquid to these wells until the disturbance blocking structure is at least partially submerged;
incubating the cells for a certain time period.
15. Method according to aspect 14, further comprising a step of:
introducing one or several pharmaceutically active substances into at least some of the wells.
16. Method according to aspect 14 or 15, wherein the step of introducing non-adherent cells (15) comprises inserting a tip of a pipette into the first chamber (111) through the through hole (123).
17. Method according to aspect 14, 15 or 16, wherein less than 20,000 cells are introduced per well, preferably less than 10,000 cells per well.
18. Method according to any of aspects 14 to 17, wherein the step of adding liquid comprises:
inserting a tip (20) of a pipette into the second chamber (112); and
injecting liquid towards the disturbance blocking structure (121) and/or towards one of the second sidewalls (104).
19. Method according to any of aspects 14 to 18, wherein the non-adherent cells (15) comprise one or any combination of cells selected from the group consisting of: blood cells, bone marrow cells, dissociated lymph node tissue, hematopoietic stem cells.
20. Method according to any of aspects 14 to 19, further comprising:
a step of staining the non-adherent cells (15), wherein one or more dyes are added to the second chamber (112); and/or
a step of fixating the non-adherent cells (15), wherein one or more fixatives are added to the second chamber (112).
21. Method according to any of aspects 14 to 20, further comprising a step of:
taking images of the non-adherent cells (15) in the multiwell plate.
22. Use of a multiwell plate according to any of aspects 1 to 13 for drug screening and/or chemosensitivity testing, preferably by performing the method according to any one of claims 14 to 21.

The invention claimed is:
1. A multiwell imaging plate for incubating monolayers of non-adherent cells, the plate including multiple wells, wherein at least some of the wells comprise:
a first chamber, the first chamber being formed by one or more first sidewalls and a bottom wall;
a second chamber, the second chamber being formed by one or more second sidewalls and including an opening for introducing liquids, wherein the second chamber is arranged on top of the first chamber;
an intermediate floor provided between the first chamber and the second chamber which forms a disturbance blocking structure;
wherein the intermediate floor is provided with at least one through hole that provides a liquid connection between the first and second chambers;
wherein the through hole extends in a vertical direction through the intermediate floor;
wherein the through hole has a width of at least 0.8 mm; and
wherein the through hole is configured for a tip of a pipette containing the non-adherent cells being inserted through the second chamber into the first chamber through said through hole.
2. Multiwell plate according to claim 1, wherein, in a top view of the respective well, the through hole is spaced from the first and from the second sidewalls.
3. Multiwell plate according to claim 1, wherein, in a top view of the respective well, the through hole is formed in the center of the well.
4. Multiwell plate according to claim 1, wherein the one or more first sidewalls are made of a dark, light absorbing material and the bottom wall is transparent.
5. Multiwell plate according to claim 1, wherein the intermediate floor protrudes into the respective well along at least a portion of the wells' periphery.
6. Multiwell plate according to claim 1, wherein the intermediate floor extends in a horizontal plane.
7. Multiwell plate according to claim 1, wherein the intermediate floor is self-supporting.
8. Multiwell plate according to claim 1, wherein an inner bottom surface of the bottom wall is flat or not microstructured.
9. Multiwell plate according to claim 1, wherein the through hole is a circular through hole having a diameter of at least 1 mm.
10. Multiwell plate according to claim 1, wherein the first chamber has a volume of 150 µL or less.
11. Multiwell plate according to claim 1, wherein the one or more first sidewalls and the one or more second sidewalls are contiguous with each other and the disturbance blocking structure is formed integrally with said first and second sidewalls.
12. Multiwell plate according to claim 11, wherein the intermediate floor is connected to and projects from the first sidewalls along at least a portion of its periphery.
13. Multiwell plate according to claim 1, wherein the disturbance blocking structure is provided by a disturbance blocking element that is inserted into or attached onto a structure forming a plurality of first chambers.
14. A method of incubating monolayers of non-adherent cells, the method including the following steps:
providing a multiwell plate according to claim 1;
introducing non-adherent cells into at least some of the wells;
adding liquid to these wells until the disturbance blocking structure is at least partially submerged;
incubating the cells for a certain time period.
15. Method according to claim 14, further comprising a step of: introducing one or several pharmaceutically active substances into at least some of the wells.
16. Method according to claim 14, wherein the step of introducing non-adherent cells comprises inserting a tip of a pipette into the first chamber through the opening of the second chamber, the second chamber, and the through hole.
17. Method according to claim 14, wherein less than 20.000 cells are introduced per well.

18. Method according to claim 14, wherein the step of adding liquid comprises:
  inserting a tip of a pipette into the second chamber; and
  injecting liquid towards the disturbance blocking structure or towards one of the second sidewalls.

19. Method according to claim 14, wherein the non-adherent cells comprise one or any combination of cells selected from the group consisting of: blood cells, bone marrow cells, dissociated lymph node tissue, hematopoietic stem cells.

20. Method according to claim 14, further comprising:
  a step of staining the non-adherent cells, wherein one or more dyes are added to the second chamber;
  a step of fixating the non-adherent cells, wherein one or more fixatives are added to the second chamber; and
  taking images of the non-adherent cells in the multiwell plate.

* * * * *